US006464982B1

(12) United States Patent
Lam (10) Patent No.: US 6,464,982 B1
(45) Date of Patent: Oct. 15, 2002

(54) HERBAL IMMUNE SYSTEM STIMULANT

(75) Inventor: Paul Y. S. Lam, Los Angeles, CA (US)

(73) Assignee: Chinese Herbal USA, Inc., Los Angeles, CA (US)

( * ) Notice: Subject to any disclaimer, the term of this patent is extended or adjusted under 35 U.S.C. 154(b) by 0 days.

(21) Appl. No.: 09/985,461

(22) Filed: Nov. 2, 2001

(51) Int. Cl.[7] .......................... A01N 65/00; A61K 35/78; A61K 9/00; A61K 9/20; A61K 39/00
(52) U.S. Cl. .................. 424/195.15; 424/725; 424/773; 424/400; 424/464; 424/184.1
(58) Field of Search ............................ 424/195.15, 725, 424/773, 400, 464, 184.1

(56) References Cited

PUBLICATIONS

Akihisa T, et al., "Triterpene Alcohols From The Flowers Of Compositae And Their Anti–Inflammatory Effects," Phytochemistry Dec. 1996;43(6):1255–1260.
Bao X, et al., "Structural And Immunological Studies Of A Major Polysaccharide From Spores Of Ganoderma Lucidum (Fr.) Karst," Carbohydr Res May 8, 2001:332(1):67–74.
Cassidy, C.M., "Chinese Medicine Users In The United States Part I: Utilization, Satisfcation, Medical Plurality," J. Alt. Comp. Med. 1998 4:17–27.
Cassidy, C.M., "Chinese Medicine Users In The United States Part II: Preferred Aspects Of Care," J. Alt. Comp. Med. 1998 4:189–202.
Cheung W.M., et al., "Ganoderma Extract Activates MAP Kinases And Induces The Neuronal Differentiation Of Rat Pheochromocytoma PC12 Cells," FEBS Lett Dec. 15, 2000:486(3):291–296.
Choate, C., "Modern Medicine and Traditional Chinese Medicine; Diabetes Mellitus, Part Three," J. Chinese Med., No. 60, May 1999.
Chu, D.T., et al., "Fractionated Extract of *Astragalus membranaceus*, a Chinese Medicinal Herb, Potentiates LAK Cell Cytotoxicity Generated By A Low Dose Of Recombinant Interleukin–2," J. Clin. Lab Immunol. 26, 183–187 (1988).
Chu, D.T., et al., "Immunotherapy with Chinese Medicinal Herbs. II. Reversal of cyclophosphamide–induced immune suppression by administration of fractionated *Astragalus membranaceus* in vivo," J. Clin. Lab. Immunol 1988 25:125–129.
de la Taille A, et al., "Role Of Herbal Compounds (PC–SPES) In Hormone–Refractory Prostate Cancer: Two Case Reports," J Altern. Complement Med Oct. 2000;6(5):449–451).
Eisenberg, D.M., et al. "Trends In Alternative Medicine Use In The United States, 1990–1997: Results Of A Follow–Up National Survey," JAMA, J. Am. Med. Assoc. 1988 280:1569–1575.
Eisenberg, D.M., et al., "Unconventional Medicine In The United States: Prevalence, Costs, And Patterns Of Use," N. Engl. J. Med. 1993 328:246–252.

Hu CQ, et al., "Anti–AIDS Agents, 10. Acacetin–7–O–beta–D–galactopyranoside, An Anti–HIV Principle From Chrysanthemum Morifolium And A Structure–Activity Correlation With Some Related Flavonoids," J. Nat. Prod. Jan. 1994 57(1):42–51.
Hu S., et al., "Influence Of Medicinal Herbs On Phagocytosis By Bovine Neutrophils," Zentralbl Veterinarmed A Oct. 1992 39(8):593–599.
Jiezhong, X., "Senile Dementia; Experience in Treatment According to Differentiation of Patterns," J. Chinese Med., No. 53, Jan. 1997.
Jin, R. and Kurashige, S., "Effects Of Chinese Herbs On Macrophage Functions In N–Butyl–N–Butanolnitrosoamine Treated Mice," Immunopharmacol Immunotoxicol 1996 18:105–114.
Kurashige, S., et al., "Effects Of Astragali Radix Extract On Carcinogenesis, Cytokine Production, And Cytotoxicity In Mice Treated With A Carcinogen, N–Butyl–N'–Butanolnitrosoamine," Cancer Invest. 1999 17:30–35.
Lee J.M., et al., "Inhibition Of Lipid Peroxidation And Oxidative DNA Damage By Ganoderma Lucidum," Phytother Res May 15, 2001(3):245–249.
MacLennan, A.H., et al., "Prevalence And Cost Of Alternative Medicine In Australia," Lancet 1996 347:569–573.
Matsuura K, et al., "Role Of B–Lymphocytes In The Immunopharmacological Effects Of A Traditional Chinese Medicine, Xiao–Chai–Hu–Tang (Shosaiko–to)," Int. J. Immunopharmacol. 1993 15:237–243.
Rittenhouse, J.R., et al., "Chinese Medicinal Herbs Reverse Macrophage Suppression Induced By Urological Tumors," J. Urol. 1991 146:486–490.
Sun, Y., et al., "Immune Restoration And/Or Augmentation Of Local Graft Versus Host Reaction By Traditional Chinese Medicinal Herbs," Cancer Invest. 1983 52:70–73.
Tomlinson, B., et al., "Toxicity Of Complementary Therapies: An Eastern Perspective," Journal Of Clinical Pharmacology 2000 40:451–456.
Ukiya M., et al., "Constituents Of Compositae Plants. 2. Triterpene Diols, Triols, And Their 3–O–Fatty Acid Esters From Edible Chrysanthemum Flower Extract And Their Anti–Inflammatory Effects," J Agric Food Chem Jul. 2001 49(7):3187–3197.

(List continued on next page.)

Primary Examiner—Christopher R. Tate
Assistant Examiner—Randall Winston
(74) Attorney, Agent, or Firm—Jeffrey I. Auerbach; Liniak, Berenato, Longacre & White, LLC (57) ABSTRACT

The invention concerns an immune system stimulator comprising *Ganoderma Lucidum, Dioscoreae Oppositae, Chrysanthemum Morifolium, Radix Astragali*, and *Folium Isatidis*. The composition is capable of mediating enhanced production of Interleukin-1 beta without causing an increase in the production of Interleukin-4.

25 Claims, 3 Drawing Sheets

OTHER PUBLICATIONS

Wang H.K., et al., "Recent Advances In The Discovery And Development Of Flavonoids And Their Analogues As Antitumor And Anti–HIV Agents," Adv Exp Med Biol 1998 439:191–225.

Yamada H, et al., "Mitogenic And Complement Activating Activities Of The Herbal Components Of Juzen–Taiho–To," Planta Med. 1992 58:166–170.

Yoshida, Y., et al., "Immunomodulating Activity Of Chinese Medicinal Herbs And Oldenlandia Diffusa In Particular," Int. J. Immunopharmacol. 1997 19:359–370.

Zhang L., et al., "Solution Properties Of Antitumor Sulfated Derivative Of Alpha–(1→3)–D–Glucan From Ganoderma Lucidum," Biosci Biotechnol Biochem Oct. 2000 64(10):2172–2178.

Zhao C, et al., "Inhibition Of The Development Of Plasmodium Yoelii In Exoerythrocytic Stage In Rodents (Rats) With Chrysanthemum Morifolium," J. Tongji Med. Univ. 1996 16(4):200–202.

Zhao C., et al., "Effect of alcohol extracts of *Chrysanthemum morifolium* on *Plasmodium falciparum* in vitro," J Tongji Med Univ 1996 16(4):203–204.

HERBAL IMMUNE SYSTEM STIMULANT

FIELD OF THE INVENTION

This invention relates to dietary supplements. More particularly, this invention relates to supplements that will stimulate the immune system without producing an allergic response.

BACKGROUND OF THE INVENTION

Recently, evidence has been accumulating that herbal supplements, taken regularly, may have beneficial effects. Herbal supplements, unlike medicines, are not effective instantaneously but must be taken over long periods of time in order to be effective. In other words, it takes time to create an effect in humans. There are many products on the market that claim to stimulate the immune system but the research behind such products seems to be borderline at best. Stimulating the immune system is a perfect application for herbal supplements because the immune system can be improved gradually. An improved immune system can be beneficial in fighting all kinds of illnesses from the common cold to deadly cancers.

Unfortunately, many herbal supplements can create an allergic response in humans. What is needed is a dietary supplement or herbal supplements that can stimulate the human immune system without inducing an allergic response. It is also important that this product have been properly tested for efficacy. Development of an herbal supplement that can stimulate the immune system without producing an allergic response presents a great improvement in the field of medicine and satisfies a long felt need of medical practitioners and of their patients.

SUMMARY OF THE INVENTION

In detail, the invention concerns an immune system stimulator composition comprising *Ganoderma Lucidum, Dioscoreae Oppositae, Chrysanthemum Morifolium, Radix Astragali*, and/or *Folium Isatidis*. The invention particularly concerns such immune system stimulator compositions wherein the compositions comprise 5–80% by weight *Ganoderma Lucidum*, 5–80% by weight *Dioscoreae Oppositae*, 5–80% by weight *Chrysanthemum Morifolium*, 1–40% by weight *Radix Astragali* and/or 1–40% by weight *Folium Isatidis*.

The invention is particularly concerned with embodiments of such compositions, wherein all of the ingredients are powdered, and/or wherein the ingredients are present in a biologically effective amount per dose (preferably containing 100 mg total amount per dose).

The invention is particularly concerned with embodiments of the above compositions in which a biologically effective amount of the ingredients are incorporated into a pill, a capsule, or a gel cap (preferably containing 100 mg total amount per dose).

The invention additionally concerns a method of making an immune system stimulator comprising the steps of:

(a) obtaining powdered *Ganoderma Lucidum, Dioscoreae Oppositae, Chrysanthemum Morifolium, Radix Astragali*, and *Folium Isatidis*; and (b) mixing 5–80% by weight *Ganoderma Lucidum*, 5–40% by weight *Dioscoreae Oppositae*, 5–40% by weight *Chrysanthemum Morifolium*, 1–40% by weight *Radix Astragali* and 5–40% by weight *Folium Isatidis* together.

The invention is particularly concerned with embodiments of the above methods wherein biologically effective amounts of the ingredients are incorporated into a pill, a capsule, or a gel cap (preferably containing 100 mg total amount per dose).

The invention further provides a method of stimulating the immune system of a human or other mammal comprising providing to the human or other mammal a biologically effective amount of an immune system stimulator comprising *Ganoderma Lucidum, Dioscoreae Oppositae, Chrysanthemum Morifolium, Radix Astragali*, and *Folium Isatidis*. The invention particularly concerns the embodiment of such method wherein the stimulator comprises 5–80% by weight *Ganoderma Lucidum*, 5–80% by weight *Dioscoreae Oppositae*, 5–80% by weight *Chrysanthemum Morifolium*, 1–40% by weight *Radix Astragali* and 1–40% by weight *Folium Isatidis*, and more particularly, wherein the stimulator comprises 10–70% by weight *Ganoderma Lucidum*, 10–70% by weight *Dioscoreae Oppositae*, 10–70% by weight *Chrysanthemum Morifolium*, 1–30% by weight *Radix Astragali* and 1–30% by weight *Folium Isatidis*. The invention particularly concerns the embodiment of such method wherein a biologically effective dose comprises 100 mg.

DESCRIPTION OF THE PREFERRED EMBODIMENTS

Herbal and other botanical products, along with other forms of complementary and alternative medicine (CAM), have become increasingly popular in the United States and other western countries (Eisenberg, D. M., et al. "Trends in alternative medicine use in the United States, 1990–1997: results of a follow-up national survey," JAMA, J. Am. Med. Assoc. 280, (1998)1569–1575; Eisenberg, D. M., et al., "Unconventional medicine in the United States: prevalence, costs, and patterns of use," N. Engl. J. Med. 328, (1993) 246–252; MacLennan, A. H., et al., "Prevalence and cost of alternative medicine in Australia," Lancet 347, (1996) 569–573). Traditional Chinese medicine (TCM) has a particularly long-standing and elaborate tradition of making medicinal botanicals an integral part of therapy. A recent survey indicates that there is growing interest in TCM, including herbal preparations, in the United States and that non-Asian populations constitute the largest user group (Cassidy, C. M., "Chinese medicine users in the United States part I: utilization, satisfaction, medical plurality," J. Alt. Comp. (1998) Med. 4, 17–27; Cassidy, C. M., "Chinese medicine users in the United States part II: preferred aspects of care," J. Alt. Comp. Med. 4, (1998)189–202).

In TCM, the use of a single plant extract is uncommon. Instead, between four and twelve plants are combined in specific proportions. It is thought that such combinations provide greater benefits because individual components enhance the activities and/or inhibit or reduce the toxicities of the other components (Tomlinson, B., et al., "Toxicity of complementary therapies: An eastern perspective," Journal of Clinical Pharmacology 40, (2000) 451–456). Mixtures of several plant extracts have, indeed, been shown to exert different—stronger, weaker, or even opposite—effects than individual plant extracts (Matsuura K, et al., "Role of B-lymphocytes in the immunopharmacological effects of a traditional Chinese medicine, Xiao-Chai-Hu-Tang (Shosaiko-to)," Int. J. Immunopharmacol. 15, (1993) 237–243; Yamada H, et al., "Mitogenic and complement activating activities of the herbal components of Juzen-taiho-to," Planta Med. 58, (1992) 166–170). However, it remains to be established which of these different effects are desirable in the conditions for which these botanical combinations are most frequently used.

The present invention comprises a mixture of five naturally occurring herbs: *Ganoderma Lucidum, Dioscoreae Oppositae, Chrysanthemum Morifolium, Radix Astragali, and Folium Isatidis*. In a preferred embodiment, the composition will be formulated to comprise all five of such herbs, and more preferably will be formulated to comprise 5–80% by weight *Ganoderma Lucidum*, 5–80% by weight *Dioscoreae Oppositae*, 5–80% by weight *Chrysanthemum Morifolium*, 1–40% by weight *Radix Astragali* and 1–40% by weight *Folium Isatidis*. The best mode for carrying out the invention comprises the following mixture: 10–70% by weight *Ganoderma Lucidum*, 10–70% by weight *Dioscoreae Oppositae*, 10–70% by weight *Chrysanthemum Morifolium*, 1–30% by weight *Radix Astragali* and 1–30% by weight *Folium Isatidis*. In the most preferred embodiment, such herbal composition will comprise Immune Stress Relief Herbal™ (ISR Herbal™) obtainable from Zen-Tech, Inc. (Los Angeles, Calif.).

Preferably, the compositions will be powdered, and more preferably will be powder size 80 (i.e., the powders were passed through a sieve with 80 holes. This is a Chinese standard used in measuring herbal powder).

The compositions of the present invention can be administered in any acceptable form such as in capsules, pressed into tablets, and made into gel caps. Gel caps are recent development in which a powder is placed in suspension in a fluid and then ease and calculated with a gel. The preferred dosage is 100 mg of the composition of the present invention, twice a day (for example, 100 mg at breakfast and 100 mg before bed).

Pharmacological and clinical applications of traditional Chinese herbs have been extensively documented. *Ganoderma Lucidum* has been used in traditional Chinese medicine for its anti-inflammatory and antioxidant activities (Lee J. M., et al., "Inhibition of lipid peroxidation and oxidative DNA damage by *Ganoderma lucidum*," Phytother Res 2001 May; 15(3):245–249; Bao X, et al., "Structural and immunological studies of a major polysaccharide from spores of *Ganoderma lucidum* (Fr.) Karst," Carbohydr Res 2001 May 8;332(1):67–74). Studies in rat cells have shown *Ganoderma Lucidum* to induce neuronal differentiation in rat cells (Cheung W. M., et al., "Ganoderma extract activates MAP kinases and induces the neuronal differentiation of rat pheochromocytoma PC 12 cells," FEBS Lett 2000 December 15;486(3):291–296). Chemopreventive activity of *Ganoderma Lucidum* has also been demonstrated (Zhang L., et al., "Solution properties of antitumor sulfated derivative of alpha-(1→3)-D-glucan from *Ganoderma lucidum*," Biosci Biotechnol Biochem 2000 October;64(10):2172–2178; de la Taille A, et al., "Role of herbal compounds (PC-SPES) in hormone-refractory prostate cancer: two case reports," J Altem Complement Med 2000 October;6(5):449–451).

*Dioscoreae Oppositae* has been used in traditional Chinese medicine for the treatment of senile dementia (Jiezhong, X., "Senile Dementia; Experience in Treatment According to Differentiation of Patterns," J. Chinese Med., No. 53, Jan. 1997). *Dioscoreae Oppositae* has also been used in the treatment of diabetes mellitus (Choate, C., "Modern Medicine and Traditional Chinese Medicine; Diabetes Mellitus, Part Three," J. Chinese Med., No. 60, May 1999).

*Chrysanthemum morifolium* is frequently used in Chinese medicinal formulae and has been reported to exert a variety of anti-inflamatory effects. Studies in mice have shown *Chrysanthemum morifolium* to have anti-inflammatory effects (Ukiya M., et al, "Constituents of compositae plants. 2. Triterpene diols, triols, and their 3-o-fatty acid esters from edible chrysanthemum flower extract and their anti-inflammatory effects," J Agric Food Chem 2001 July;49(7):3187–3197; Zhao C., et al., "Effect of alcohol extracts of *Chrysanthemum morifolium* on *Plasmodium falciparum* in vitro," J Tongji Med Univ 1996; 16(4):203–204; Zhao C, et al., "Inhibition of the development of Plasmodium yoelii in exoerythrocytic stage in rodents (rats) with *Chrysanthemum Morifolium*," J. Tongji Med. Univ. 1996; 16(4):200–202; Akihisa T, et al., "Triterpene alcohols from the flowers of compositae and their anti-inflammatory effects," Phytochemistry 1996 December;43(6):1255–1260). Anti-tumor and anti-HIV activity of *Chrysanthemum Morifolium* have also been demonstrated (Wang H. K., et al., "Recent advances in the discovery and development of flavonoids and their analogues as antitumor and anti-HIV agents," Adv Exp Med Biol 1998;439:191–225; Hu C Q, et al., "Anti-AIDS agents, 10. Acacetin-7-O-beta-D-galactopyranoside, an anti-HIV principle from *Chrysanthemum morifolium* and a structure-activity correlation with some related flavonoids," J. Nat. Prod. 1994 January;57(1):42–51).

*Radix Astragali* is found in numerous Chinese herbal formulae, as it is considered a tonic that can strengthen natural host immune responses. Animal studies have shown that Astragalus can restore a variety of immune functions in situations where the host immune response is depressed due to tumors, cyclophosphamide or radiation treatment, or aging. In particular, macrophage oxidative burst (Rittenhouse, J. R., et al., "Chinese medicinal herbs reverse macrophage suppression induced by urological tumors," *J Urol.*, 146, 486–490 1991), chemotaxis, and cytokine production (Jin, R. and Kurashige, S., "Effects of Chinese herbs on macrophage functions in N-butyl-N-butanolnitrosoamine treated mice," *Immunopharmacol Immunotoxicol* 18, 105–114 1996), lymphocyte IL-2 and IFN-γ production as well as cytotoxic activity (Kurashige, S., et al., "Effects of astragali radix extract on carcinogenesis, cytokine production, and cytotoxicity in mice treated with a carcinogen, N-butyl-N'-butanolnitrosoamine," *Cancer Invest*. 17, 30–35 (1999)), graft versus host (GVH) reaction (Chu, D.T., et al., "Fractionated extract of Astragalus membranaceus, a Chinese medicinal herb, potentiates LAK cell cytotoxicity generated by a low dose of recombinant interleukin-2, " *J Clin. Lab Immunol*. 26, 183–187(1988); Chu, D. T., et al., "Immunotherapy with Chinese medicinal herbs. II. Reversal of cyclophosphamide-induced immune suppression by administration of fractionated *Astragalus membranaceus* in vivo," *J. Clin. Lab. Immunol* 25, (1988) 125–129; Sun, Y., et al., "Immune restoration and/or augmentation of local graft versus host reaction by traditional Chinese medicinal herbs," *Cancer Invest*. 52, 70–73 (1983)), and T-cell dependent antibody responses (Zhao et al., 1990) were reported to be normalized to the levels seen in immune-competent controls by crude extracts and/or fractions of *A. membranaceus*.

*Folium Isatidis* herbal preparations have been categorized as antipyretics in Chinese medicine due to their ability to inhibit phagocytosis (Hu S., et al., "Influence of medicinal herbs on phagocytosis by bovine neutrophils," Zentralbl Veterinarmed A 1992 October;39(8):593–599).

In the present study, the combined effects of five herbal ingredients: *Ganoderma Lucidum, Dioscoreae Oppositae* (*Dioscoreae rhizoma*), *Chrysanthemum morifolium, Radix astragali* (*Astragalus membranaceus* (Fisch.), *Folium Isatidis*, are investigated. To do this, the product Immune Stress Relief Herbal™ (ISR Herbal™) (Zen Tech, Inc., Los Angeles, Calif.), which contains these five ingredients is employed.

This invention was tested by the following procedure at the Department Of Clinical Immunology at the University of California at Davis. California:

1. Collect blood;
2. Isolate white blood cells;
3. Isolate lymphocytes;
4. Incubate leukocytes in mini tubes for varying periods of time in the presence or absence of the composition of the present invention;
5. Incubate the lymphocytes with four serial ten-fold dilutions of the composition of the present invention from 0.1 to 100 μg/ml;
6. Repeat the same experiments in the presence or absence of phytohemagglutinin (PHA), a known as stimulator of cells;
7. Collect the culture supernatants (i.e., the fluid above the lymphocytes);
8. Using known standards and a reference curve, assay the supernatants for Interleukin 1 (IL-1) beta and Interleukin 4 (IL-4);

The results showed an impressive production of IL-1 beta without an increase in IL-4. Such production would be helpful during periods of needed immune response, i.e., during a cold or infection.

Having now generally described the invention, the same will be more readily understood through reference to the following examples, which are provided by way of illustration, and are not intended to be limiting of the present invention, unless specified.

EXAMPLE 1

In Vitro Analysis of Herbal Product

Treatment preparation. 10 mg of Immune Stress Relief Herbal™ (ISR Herbal™) (Zen-Tech, Inc.; Los Angeles, Calif.) is suspended in 1 ml of RPMI-1640 culture medium supplemented with 10% heat inactivated fetal bovine serum (media). The suspension is shaken vigorously on a vortex mixer. The insoluble components are quickly pelleted and the remaining suspension is filtered twice: first through a 0.45 micron syringe filter, and then through a 0.2 micron syringe filter. This filtrate is used as the stock solution (approximately 10 mg/ml) from which dilutions are made for the incubations with peripheral blood mononuclear cells (PBMC). The stock solution is diluted in media prior to treatment with PBMC.

PMBC Isolation. Peripheral blood from six healthy volunteers is collected and the PBMC isolated over a density gradient via centrifugation. The cells are re-suspended in RPMI-1640 medium containing 10% fetal bovine serum and supplemented with 0.1% of a 50 mg/ml gentamicin solution (Gibco BRL, Grand Island Nebr.). PBMC concentration was adjusted to $2 \times 10^6$ viable cells/ml after estimation of viability by trypan blue exclusion assay. Viability is consistently greater than 96%.

Culture of PBMC with Herbal Products. Five hundred ml of a $1.0 \times 10^6$ cell suspension are cultured with equal volume of the product treatments at 37° C. with 5% carbon dioxide in 48-well plates. PBMCs are exposed to a final concentration of 100, 10, 1, or 0.1 mg/ml of product. In addition, each product treatment is incubated in the presence of PHA at 10 mg/ml. Culture supernatants fractions are harvested after 72 hours and are stored at −20° C. until analysis by enzyme linked immunoassay (ELISA).

ELISA Analysis of Cytokines. Levels of IL-1, IL-4 and gamma interferon (IFN) are measured in supernatants from $1.0 \times 10^6$ cells/ml stimulated with product in the presence or absence of PHA. For quantitation of secretory IL-4, a high sensitivity Quantikine Human IL-4 ELISA kit is used with the detection limit of 0.25 pg/ml (R&D systems, Minneapolis, Minn.). Standard ELISA kits are used to quantitate IL-1 and IFN (R&D systems, Minneapolis, Minn.) with detection limits of 3.9 and 31.2 pg/ml respectively.

Results will show an increase of IL-1 beta of between 6 and 11 times without any increase in IL-4. In other words, the results will show that this product stimulates the human immune system without stimulating IL-4, a precursor to allergies in the human body. The testing is conducted by M. Eric Gershwin, M. D., The Jack and Donald Chia Professor of Medicine, Chief, Division of Rheumatology, Allergy, and Clinical Immunology, University of California, Davis.

EXAMPLE 2

Investigation of the Effects of a Combination of Traditional Chinese Botanicals (Immune Stress Relief Herbal™) on the Secretion of Interleukin-1β and Interferon-γ by Peripheral Blood Mononuclear Cells The use of herbal and other botanical products, including those used extensively in traditional Chinese medicine (TCM), has increased dramatically in the last decade. Yet, little scientific research exists concerning their efficacy and safety. The effects of Immune Stress Relief Herbal™ (ISR Herbal™) obtainable from Zen-Tech, Inc. (Los Angeles, Calif.), a novel combination of five botanicals frequently used in traditional Chinese medicine, on the production of two cytokines is examined. For this purpose, unstimulated or phytohemagglutinin (PHA)-stimulated peripheral blood mononuclear cells (PBMC) from healthy volunteers are incubated with different concentrations of Immune Stress Relief Herbal™ (ISR Herbal™). The secretion of interleukin (IL)-1β and interferon (IFN)-γ is measured after 72 h of incubation. At the highest concentration tested (100 μg/ml), Immune Stress Relief Herbal™ (ISR Herbal™) significantly increased the secretion of IL-1β. Importantly, PHA alone had no effect on IL-1β production, and the combination of PHA with Immune Stress Relief Herbal™ (ISR Herbal™) resulted in the same increase in IL-1β production as seen with the botanical extract alone. Immune Stress Relief Herbal™ (ISR Herbal™) did not have any detectable effect on either unstimulated or PHA-stimulated IFN-γ synthesis. These in vitro data support the concept that the herbal compositions of the present invention may enhance human immune responses.

Although the five ingredients being tested are frequently found in TCM, their combined formulation in the compositions of the present invention (as in Immune Stress Relief Herbal™ (ISR Herbal™)) is not one of the standard formulae of TCM. Therefore, no research has previously been conducted on this particular combination of botanicals, although data are available on most of the individual ingredients.

Interferon-γ is important in determining the differentiation of CD4 T cells into Th1 rather than Th2 T cells (Boehm, U., et al., "Cellular responses to interferon-g," Annu. Rev. Immunol. 15, (1997) 749–795.) and thereby exerts a vital influence on the host response not only to viral and bacterial infections but also to tumors. Several of the ingredients of Immune Stress Relief Herbal™ (ISR Herbal™) have been reported to influence the production of IFN-γ, and almost all are used in the treatment of cancer patients. Therefore, the effect of the compositions of the present invention on the in vitro synthesis of this cytokine by unstimulated and stimulated PBMC from healthy volunteers was investigated. Immune Stress Relief Herbal™ (ISR Herbal™)) was used for this investigation. The existing data also indicates that ingredients of the compositions of the present invention stimulate the non-adaptive arm of the immune system, particularly macrophages. IL-1β is not only produced by activated macrophages but further stimulates them. Yet, little data exists on the effects of any of the ingredients of the compositions of the present invention on the production of this cytokine. The effect of the compositions of the present invention on IL-1β synthesis by unstimulated and stimulated PBMC is therefore examined using Immune Stress Relief Herbal™ (ISR Herbal™)).

Materials and Methods

Stock Solution

Ten mg of Immune Stress Relief Herbal™ (ISR Herbal™)) (Zen-Tech, Inc.; Los Angeles, Calif.) is suspended in 1 ml RPMI-1640 with 10% heat inactivated fetal bovine serum (media). The suspension is shaken vigorously on a vortex mixer. The insoluble components are quickly pelleted and the remaining suspension is filtered twice: first through a 0.45 micron syringe filter followed by a 0.2 micron syringe filter. This filtrate is used as our stock (approx. 10 mg/ml) from which dilutions are made for the incubations with PBMC. The stock solution is diluted in media prior to treatment with PBMC.

Peripheral Blood Mononuclear Cell (PBMC) Isolation

Volunteers of various ethnic backgrounds and ranging in age from 18–35 years, participate in this study. Peripheral blood is collected into sodium citrate-containing tubes and mixed 1:1 with Hanks' Balanced Salt Solution (HBSS; Gibco BRL, Gaithersburg, Md.) without calcium chloride, magnesium chloride, or magnesium sulfate. The diluted blood is then layered over an Accu-Paque gradient (Accurate Chemical and Scientific Corp., Westbury, N.Y.) and is centrifuged at 500 g for 30 minutes at room temperature. PBMC are harvested from the interface layer, washed twice with HBSS. The cells are resuspended in RPMI 1640 (Gibco BRL) containing 10% fetal bovine serum and supplemented with 0.1% of a 50 mg/ml gentamicin solution (Gibco BRL). The PBMC concentration is adjusted to $2 \times 10^6$ viable cells per milliliter. Viability is determined by trypan blue exclusion and was consistently >96%. All data is verified by at least three separate experiments.

Culture of PBMC with Immune Stress Relief Herbal™ (ISR Herbal™))

Five hundred microliters of this $2.0 \times 10^6$ cell suspension, i.e., $1.0 \times 10^6$ cells, are cultured in 48-well plates with an equal volume of each of the four concentrations of Immune Stress Relief Herbal™ (ISR Herbal™)) in the presence or absence of phytohemagglutinin (PHA) at a final concentration of 10 μg/ml. All treatments are performed in duplicate. After incubation at 37° C. in 5% $CO_2$ for 72 h, the supernatant fractions are harvested for enzyme-linked immunosorbent assay (ELISA) analysis.

ELISA Analysis of L-1β and IFN-γ

Aliquots of culture supernatants are frozen immediately upon harvest and are stored at −20° C. until analysis by ELISA. Concentrations of IL-1β and IFN-γ are determined using the DuoSet® ELISA Development System (R & D Systems, Minneapolis, Minn.) with a detection limit of 3.9 and 15.6 pg/ml respectively.

Statistics

The effects of various concentrations of Immune Stress Relief Herbal™ (ISR Herbal™)) on IL-1β and IFN-γ production in either unstimulated or PHA-stimulated PBMC are analyzed using a one-way ANOVA followed by post-hoc Tukey comparison. The results are presented as means±standard error of the mean (SEM). Results are considered statistically significant when $p < 0.001$.

Results

PBMC from healthy volunteers are incubated for 72 h with either media alone (control), four different concentrations of Immune Stress Relief Herbal™ (ISR Herbal™)), or the same concentrations of Immune Stress Relief Herbal™ (ISR Herbal™)) together with 10 μg/ml of PHA. The concentrations of IL-1β and IFN-γ in the supernatant are measured by ELISA.

Figure 1:
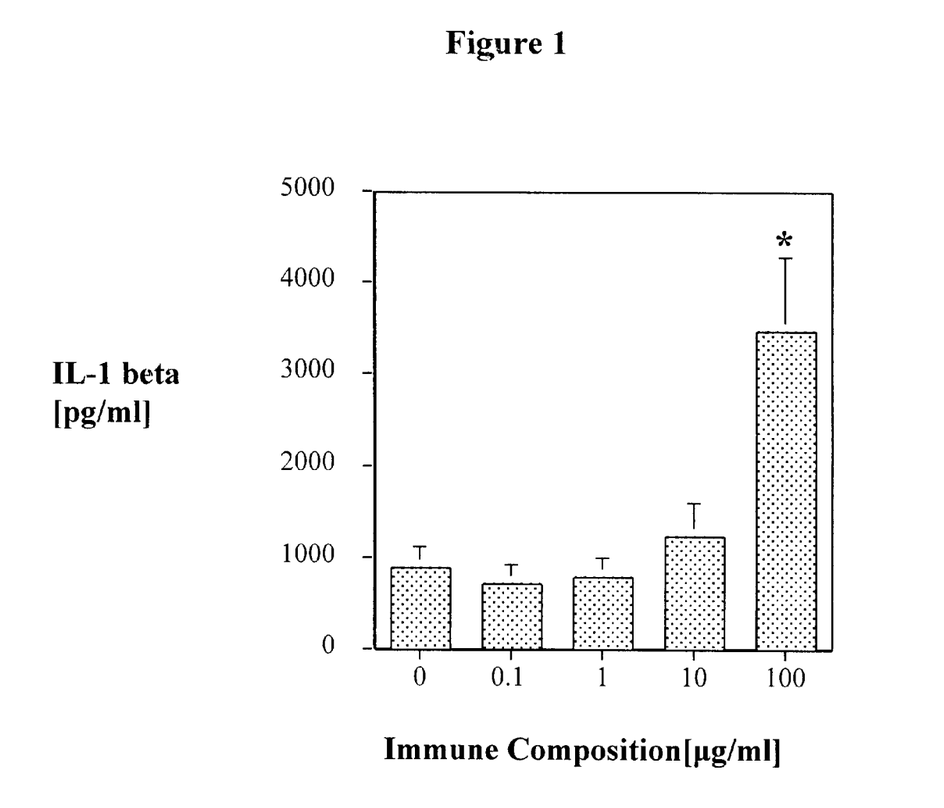
FIG. 1 illustrates the effect of four different concentrations of a preferred composition of the present invention on the secretion of IL-1β following a 72 h incubation with PBMCs. Data are shown as concentration of IL-1β in pg/ml (mean±sem; n=10). * indicates statistical significance compared to media control, where $p<0.001$.
Figure 2:
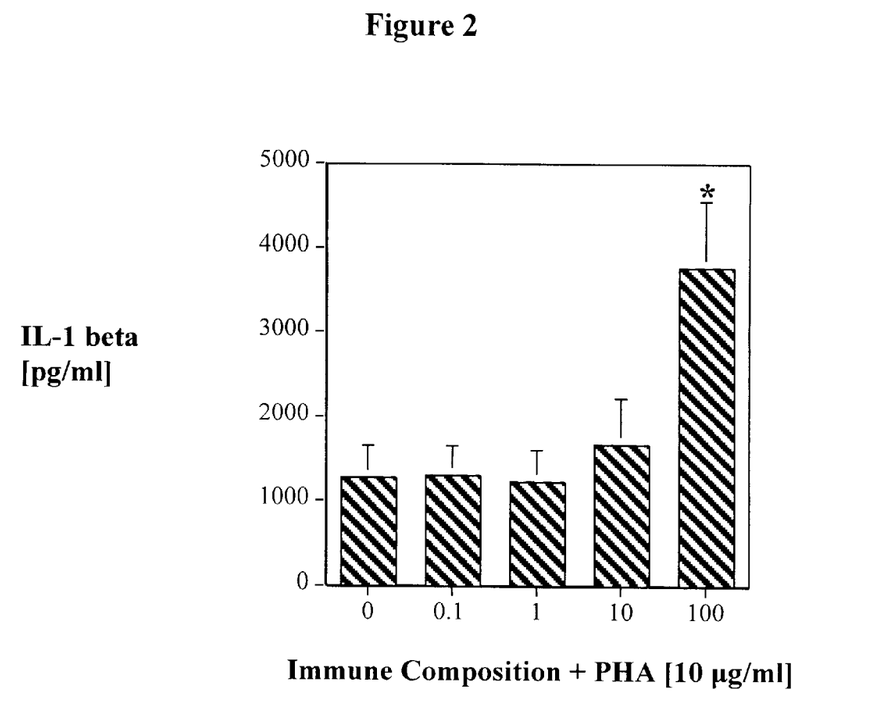
FIG. 2 shows the effect of four different concentrations of a preferred composition of the present invention combined with 10 μg/ml of PHA on the secretion of IL-1β following a 72 h incubation with PBMC. Data are shown as concentration of IL-1β in pg/ml (mean±sem; n=10). * indicates statistical significance compared to PHA control, where $p<0.001$.

The effects of the compositions of the present invention on IL-1β synthesis. In the absence of PHA, a 72-h incubation of PBMC with Immune Stress Relief Herbal™ (ISR Herbal™)) at 100 μg/ml significantly increases the production of IL-1β from a mean of about 900 pg/ml in the media control to a mean of about 3460 pg/ml (see FIG. 1). This represents an average change of 317±73% (range: 104–832%, Table 1). No significant changes compared to the media control are observed at any of the lower concentrations (10, 1, and 0.1 μg/ml) of Immune Stress Relief Herbal™ (ISR Herbal™)), although some individuals do show marked increases. Three subjects, whose cells are exposed to a concentration of 10 μg/ml, display a 55–115% increase in IL-1β production. Addition of PHA at 10 μg/ml has little effect on herbal-induced IL-1β synthesis (Table 1). The same concentration of PHA in combination with 100 μg/ml of Immune Stress Relief Herbal™ (ISR Herbal™)) results in a similar increase of IL-1β production as that seen with Immune Stress Relief Herbal™ (ISR Herbal™)) alone (see FIG. 2). Although the combination of PHA and Immune Stress Relief Herbal™ (ISR Herbal™)) at 10 μg/ml results in higher IL-1β synthesis compared to PHA alone, this increase does not reach statistical significance. The other two concentrations of Immune Stress Relief Herbal™ (ISR Herbal™)) have no detectable effect on IL-1β synthesis compared to the results obtained with PHA alone.

TABLE 1

The percentage change of IL-1 beta production. PBMCs treated with only Immune Stress Relief Herbal ™ (ISR Herbal ™) are compared to media IL-1 beta levels, while cells co-incubated with PHA (at 10 μg/ml) are compared to PHA control.
Data represents mean % change ± SEM (n = 10)

| Group | Dose [μg/ml] | % Change |
|---|---|---|
| Immune Stress Relief Herbal ® (ISR Herbal ®) only | 0 | — |
|  | 0.1 | −30 ± 6 |
|  | 1 | −22 ± 7 |
|  | 10 | 18 ± 15 |
|  | 100 | 317 ± 73 |
| Immune Stress Relief Herbal ® (ISR Herbal ®) + PHA | 0 | — |
|  | 0.1 | 11 ± 10 |
|  | 1 | −5.4 ± 5 |
|  | 10 | 27 ± 12 |
|  | 100 | 312 ± 109 |

Figure 3:
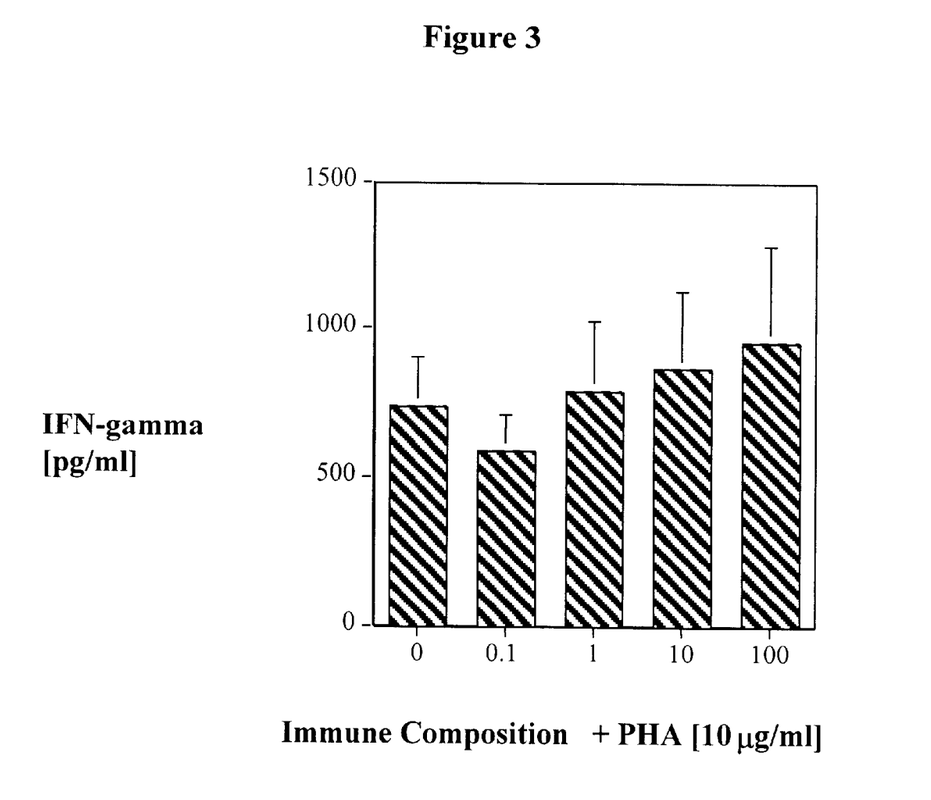
FIG. 3 shows the effect of four different concentrations of a preferred composition of the present invention co-incubated with 10 μg/ml of PHA on the secretion of IFN-gamma following a 72 hour incubation with PBMC. Data are shown as concentration of IFN-gamma in pg/ml (mean±sem; n=8).

The effect of the present invention on secretion of IFN-γ was investigated. IN the absence of PHA, little or no IFN-γ is detectable in the supernatant of PBMC cultured for 72 h with either media only (control) or with various concentrations of Immune Stress Relief Herbal™ (ISR Herbal™). Thus, under the present experimental conditions, the composition of the present invention alone do not enhance the synthesis of IFN-γ in PBMC from healthy volunteers. Incubation of PBMC with PHA at a concentration of 10 μg/ml for 72 h results in a production of IFN-γ. The compositions of the present invention do not significantly affect the PHA-induced synthesis of IFN-γ at any of the concentrations tested (see FIG. 3, Table 2). However, PBMC from two subject treated at the highest concentration, are able to augment IFN-γ production by 150% of PHA control.

TABLE 2

The percentage change of IFN-gamma production. PBMCs treated with the compositions of the present invention in the presence of PHA (at 10 μg/ml) are compared to PHA control.
Data represents mean % change ± SEM (n = 8)

| Group | Dose [μg/ml] | % Change |
|---|---|---|
| Immune Stress Relief Herbal ® (ISR Herbal ® ) + PHA | 0 | — |
|  | 0.1 | −16 ± 11 |
|  | 1 | 4.8 ± 18 |
|  | 10 | 12 ± 19 |
|  | 100 | 24 ± 30 |

The compositions of the present invention comprise a dietary supplement of the extracts of 5 botanicals frequently used in TCM, namely *Ganoderma Lucidum, Dioscoreae Oppositae, Chrysanthemum Morifolium, Radix Astragali, Polium Isatidis*. Individually, these botanicals have been shown to exert immunomodulatory effects, but it has not been previously investigated whether and how their combination can influence immune responses. The above reported experiment demonstrates that the compositions of the present invention at 100 μpg/ml, significantly increases the secretion of IL-1β by PBMC from healthy volunteers. The combination of the compositions of the present invention with PHA results in the same concentrations of IL-1β as those obtained with Immune Stress Relief Herbal™ (ISR Herbal™) alone. Little is known about the ability of the other ingredients of the compositions of the present invention to affect IL-1β production. In addition, the extract from a single plant or plant part often exerts different immunomodulatory effects than when it is combined with other plant extracts. It can, therefore, not be determined which ingredient(s) or specific combination of ingredients present in the compositions of the present invention is responsible for the unexpected results in the enhancement of IL-1β production observed. Moreover, the compositions of the present invention do not significantly alter the synthesis of IFN-γ by either unstimulated or PHA-stimulated PBMC.

The i.p. administration of glycyrrhizin to mice is found to induce CD4 T cells capable of producing significant amounts of IFN-γ upon stimulation with anti-CD3 antibodies. In addition, *Radix Astragali* has been reported to upregulate the IFN-γ production of mice whose immune functions were suppressed due to the presence of chemically induced tumors (Kurashige et al., 1999). Based on these data, the compositions of the present invention might have been expected to result in an upregulation of IFN-} synthesis at least in the presence of PHA. It is also not known what effect, if any, the other ingredients of the compositions of the present invention have on IFN-γ production. It is possible that they contain substances that inhibit the IFN-γ inducing activity of glycyrrhizin and *Radix Astragli*.

The present data allow some extrapolation as to what the in vivo effects of the consumption of the compositions of the present invention might be. If it upregulates IL-1β synthesis in vivo to a similar extent as it does in vitro, it might offer benefit against infectious diseases in which the non-adaptive arm of the immune system plays a vital role.

*Radix Astragali* is found in numerous Chinese herbal formulae, as it is considered a tonic that can strengthen natural host immune responses. Animal studies have shown that Astragalus can restore a variety of immune functions in situations where the host immune response is depressed due to tumors, cyclophosphamide or radiation treatment, or aging. In particular, macrophage oxidative burst (Rittenhouse et al., 1991), chemotaxis, and cytokine production (Jin et al., 1996), lymphocyte IL-2 and IFN-γ production as well as cytotoxic activity (Kurashige et al., 1999), graft versus host (GVH) reaction (Chu et al., 1988, Sun et al., 1983), and T-cell dependent antibody responses (Zhao et al., 1990) were reported to be normalized to the levels seen in immune-competent controls by crude extracts and/or fractions of *A. membranaceus*.

In vitro, a partially purified fraction of *A. membranaceus* resulted in a 10-fold potentiation in the ability of low doses of recombinant IL-2 to induce LAK activity (Chu et al., 1988). *A. membranaceus* also increased mouse spleen cell proliferation, polyclonal Ig production, macrophage tumor necrosis factor (TNF) and IL-6 activity, as well as cytotoxic T cell, but not NK cell, activity in vitro (Yoshida, Y., et al., "Immunomodulating activity of Chinese medicinal herbs and Oldenlandia diffusa in particular," Int J Immunopharmacol 19, (1997) 359–370). Others, however, observed a slight, but statistically significant decrease in IL-6 synthesis by mouse splenocytes incubated with *A. membranaceus*, and reported reduced IgG2a production during the primary, but not the secondary, immune response, while IgGI was unaffected (Song, Q. H., et al., "Effects of Astragali root and Hedysari root on the murine B and T cell differentiation," J. Ethnopharmacol 73, (2000)111–119).

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A pharmaceutical composition comprising an immune system stimulator composition, said immune system stimulator composition comprising a biologically effective amount of herbs, or extracts thereof, of: *Ganoderma Lucidum, Dioscoreae Oppositae, Chrysanthemum Morifolium, Radix Astragali*, and *Folium Isatidis*.

2. The pharmaceutical composition of claim 1, wherein said herbs or extracts thereof of said immune system stimulator composition comprise 5–80% by weight *Ganoderma Lucidum*, 5–80% by weight *Dioscoreae Oppositae*, 5–80% by weight *Chrysanthemum Morifolium*, 1–40% by weight *Radix Astragali* and 1–40% by weight *Folium Isatidis*.

3. The pharmaceutical composition of claim 1, wherein said herbs or extracts thereof of said immune system stimulator composition comprise 40–70% by weight *Ganoderma Lucidum*, 10–50% by weight *Dioscoreae Oppositae*, 5–30% by weight *Chrysanthemum Morifolium*, 1–30% by weight *Radix Astragali* and 5–30% by weight *Folium Isatidis*.

4. The pharmaceutical composition of any of claims 1, 2 or 3, wherein said herbs or extracts thereof of said immune system stimulator composition are powdered.

5. The pharmaceutical composition of claim 4, wherein said pharmaceutical composition is incorporated into a pill.

6. The pharmaceutical composition of claim 4, wherein said pharmaceutical composition is incorporated into a capsule.

7. The pharmaceutical composition of claim 4, wherein said pharmaceutical composition is incorporated into a gel cap.

8. The pharmaceutical composition of claim 1, wherein said herbs or extracts thereof of said immune system stimulator composition are powdered and a biologically effective amount thereof is incorporated into a pill, capsule, or gel cap.

9. The pharmaceutical composition of claim 8, wherein said biologically effective amount of said immune system stimulator composition is 100 mg per dose.

10. The pharmaceutical composition of claim 2, wherein said herbs or extracts thereof of said immune system stimulator composition are powdered and a biologically effective amount thereof is incorporated into a pill, capsule, or gel cap.

11. The pharmaceutical composition of claim 10, wherein said biologically effective amount of said immune system stimulator composition is 100 mg per dose.

12. The pharmaceutical composition of claim 3, wherein said herbs or extracts thereof are powdered and a biologically effective amount thereof is incorporated into a pill, capsule, or gel cap.

13. The pharmaceutical composition of claim 12, wherein said biologically effective amount of said immune system stimulator composition is 100 mg per dose.

14. A method of making an immune system stimulator composition comprising the steps of:

(a) obtaining powdered *Ganoderma Lucidum, Dioscoreae Oppositae, Chrsanthemum Morifolium, Radix Astragahi*, and *Folium Isaridis*; and (b) mixing 5–80% by weight *Ganodenna Lucidum*, 540% by weight *Dioscoreae Oppositae*, 5–40% by weight *Chrysanthemum Morifolium*, 1–40% by weight *Radix Astragali* and 5–40% by weight *Folium Isatidis* together.

15. The method of claim 14, wherein the mixture formed in said step (b) comprises 10–70% by weight *Ganoderma Lucidum*, 10–70% by weight *Dioscoreae Oppositae*, 10–70% by weight *Chrysanthemum Morifolium*, 1–30% by weight *Radix Astragali* and 1–30% by weight *Folium Isatidis*.

16. The method of any of claims 14 or 15, wherein method further comprises formulating said mixture into a pill.

17. The method of claim 16, wherein said pill contains 100 mg of said mixture.

18. The method of any of claims 14 or 15, wherein method further comprises formulating said mixture into a capsule.

19. The method of claim 18, wherein said capsule contains 100 mg of said mixture.

20. The method of any of claims 14 or 15, wherein method further comprises formulating said mixture into a gel cap.

21. The method of claim 20, wherein said gel cap contains 100 mg of said mixture.

22. A method of stimulating the immune system of a human or other mammal comprising providing to said human or other mammal a pharmaceutical composition comprising an immune system stimulator composition, said immune system stimulator composition comprising a biologically effective amount of herbs, or extracts thereof, of; *Ganoerma Lucidum, Dioscoreae Oppositae, Chrysanthemum Morifolium, Radix Astragali*, and *Folium Isatidis*.

23. The method of stimulating the immune system of a human or other mammal of claim 22, wherein said biologically effective amount of herbs or extracts thereof of said immune system stimulator composition comprises 5–80% by weight *Ganoderma Lucidum*, 5–40% by weight *Dioscoreae Oppositae*, 5–40% by weight *Chrysanthemum Morifolium*, 1–40% by weight *Radix Astragali* and 5–40% by weight *Folium Isatidis*.

24. The method of stimulating the immune system of a human or other mammal of claim 23, wherein said biologically effective amount of herbs or extracts thereof of said immune system stimulator composition comprises 40–70% by weight *Ganoderma Lucidum*, 10–50% by weight *Dioscoreae Oppositae*, 5–30% by weight *Chrysanthemum Morifolium*, 1–30% by weight *Radix Astragali* and 5–30% by weight *Folium Isatidis*.

25. The method of stimulating the immune system of a human or other mammal of any of claims 22–24, wherein said biologically effective amount of said immune system stimulator composition is 100 mg per dose.

* * * * *